United States Patent
Damer et al.

[11] Patent Number: 6,160,625
[45] Date of Patent: *Dec. 12, 2000

[54] LASER SCANNER PROJECTION SYSTEM FOR VIEWING FEATURES ON SUBSTRATES AND ON COATED SUBSTRATES

[75] Inventors: Lewis S. Damer, St. Paul, Minn.; Justin B. Stec, Medford; William T. McArdle, White City, both of Oreg.

[73] Assignee: Eastman Kodak Company, Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/200,666

[22] Filed: Nov. 25, 1998

[51] Int. Cl.⁷ .................................................. G01N 21/32
[52] U.S. Cl. ..................... 356/430; 356/431; 250/559.06
[58] Field of Search .................... 356/429, 430, 356/431, 237.1, 239.1, 239.2, 239.7; 250/559.01, 559.02, 559.06, 559.05, 559.16, 559.49, 559.11

[56] References Cited

U.S. PATENT DOCUMENTS

| | | | |
|---|---|---|---|
| 2,247,047 | 6/1941 | Bishop, Jr. | 356/239.1 |
| 4,134,684 | 1/1979 | Jette | 356/430 |
| 4,341,469 | 7/1982 | Gardiner et al. | 356/239.1 |
| 4,643,127 | 2/1987 | Wanke | 118/413 |
| 4,714,340 | 12/1987 | Stillwagon | 356/23 |
| 4,977,852 | 12/1990 | Ishizuka | 118/411 |
| 4,982,104 | 1/1991 | Yuito | 356/430 |
| 5,071,514 | 12/1991 | Francis | 356/429 |
| 5,387,978 | 2/1995 | Okafuji et al. | 356/431 |
| 5,639,305 | 6/1997 | Brown et al. | 118/410 |
| 5,654,031 | 8/1997 | Delmore et al. | 427/8 |
| 5,741,549 | 4/1998 | Maier et al. | 427/294 |

OTHER PUBLICATIONS

"Modern Coating and Drying Technology" Editors Edward Cohen and Edgar B. Gutoff,*Published by VCH Publishers, Inc.* (1992) pp. v–310.

*Primary Examiner*—Hoa Q. Pham
*Attorney, Agent, or Firm*—Mark G. Bocchetti

[57] ABSTRACT

An inspection system for viewing substrate or coated substrate features, wherein a directed light source is projected through a coated substrate onto a viewing surface such that features or irregularities in the substrate or in the coating of the coated substrate are displayed. The inspection system includes a projection system including a light source positioned adjacent the second major surface of the optically transmissive substrate, and a viewing screen positioned adjacent the first major surface of the substrate. The substrate is positioned in optical alignment along an optical path between the light source and the viewing screen such that irregularities in the coated top surface of the substrate can be visually observed on the viewing screen by a user. In one aspect the substrate is coated. Optionally, the directed light source is a laser scanner assembly.

42 Claims, 3 Drawing Sheets

LASER SCANNER PROJECTION SYSTEM FOR VIEWING FEATURES ON SUBSTRATES AND ON COATED SUBSTRATES

TECHNICAL FIELD

The present invention generally relates to a method and apparatus for viewing surface features of a substrate or coated substrate (web) in a manufacturing process, and in particular, to an inspection system wherein a directed light source is projected through a substrate or a coated substrate onto a viewing surface such that features or irregularities in the substrate or coated substrate are displayed on the viewing surface.

BACKGROUND OF THE INVENTION

Methods and apparatus for making a substrate or applying a coating over a substrate (i.e., web coating) are employed in the manufacture of a wide variety of goods. In one example, substrate coating is commonly used in the manufacture of photothermographic, photographic, and thermographic film. Other types of goods which are manufactured by a web coating process include: pressure sensitive adhesive tapes, coated paper, magnetic audio, video and storage tapes, as well as other products.

The production of high quality articles, particularly photothermographic, photographic, and thermographic articles, consists of applying a thin film of a coating solution onto a continuously moving substrate or web. This film can be applied using a variety of techniques including dip coating, forward and reverse roll coating, gravure coating, wire wound rod coating, blade coating, slot coating, slide coating, and curtain coating. Coatings can be applied as a single layer or as two or more superimposed layers. Although it is usually most convenient for the substrate to be in the form of a continuous web, it may also be in the form of a succession of discreet sheets.

In some instances, the coating on the substrate will tend to streak as a result of problems during the coating process. This non-uniform streaking of the coating material will often render portions of the coated substrate unusable. Since the coating process is a very high-speed process, it becomes imperative to detect any streaks in the coated substrate as soon as possible in order to minimize the amount of unusable product. By performing an inspection at the end of the manufacturing process, as much as 1000 linear feet (or more) of defective product may already be manufactured by the time the defect is discovered.

Detecting any non-uniformities in the coated substrate during the manufacturing process can be very difficult. In the case of the manufacture of photosensitive coated substrates (e.g., photothermographic and photographic film), the manufacturing process is preformed under safe light conditions, where a relatively clear, somewhat diffusing coating is applied to a clear substrate. These safe light conditions make any sort of visual inspection very difficult.

SUMMARY OF THE INVENTION

The present invention is directed toward a manufacturing system having an inspection system for viewing substrate and coated substrate features.

In one embodiment, the present invention provides an inspection system for viewing substrate features in a manufacturing process, where the substrate is an optically transmissive substrate having a first major surface and second major surface. The inspection system includes a projection system including a light source positioned adjacent the second major surface, and a viewing screen positioned adjacent the first major surface. The substrate is positioned in optical alignment along an optical path between the light source and the viewing screen, wherein irregularities in the surface can be visually observed on the viewing screen by a user.

In one aspect, the optically transmissive substrate is transparent. The first system further includes an optically transmissive coating disposed over the first major surface of the optically transmissive substrate, forming a coated substrate. In one aspect, the optically transmissive coating is wet. In another aspect, the optically transmissive coating is dry. In one aspect, the optically transmissive coating is photosensitive. In one preferred embodiment, the light source is an optical scanner assembly.

In another embodiment, the manufacturing system of the present invention includes an optically transmissive substrate having a first major surface and a second major surface. The manufacturing system also includes an optically transmissive coating disposed over the first major surface of the optically transmissive substrate, forming a coated substrate. Finally, the manufacturing system includes a projection system including a light source positioned adjacent the second major surface of the substrate, and a viewing screen positioned adjacent the first major surface of the substrate. The coated substrate is positioned in optical alignment along an optical path between the light source and the viewing screen such that irregularities in the substrate or the top surface of the coated substrate can be visually observed on the viewing screen by a user.

In one embodiment of the manufacturing system of the present invention, the optically transmissive substrate is made of transparent material, and the optically transmissive coating is translucent. The manufacturing system of the present invention works with uncoated substrate and both wet and dry coatings on the substrate. The light source employed within the projection system has a wavelength and intensity that does not interfere with the photosensitive qualities of the optically transmissive coating. In one embodiment of the present invention, the light source is a point light source, such as a laser.

A preferred embodiment of the inspection system also includes a light focusing and shaping mechanism located along the optical path between the light source and the coated substrate. In one embodiment the light focusing and shaping mechanism is a set of one or more optical lenses, such as a double complex lens.

The inspection system of the present invention may also include a light redirecting mechanism having at least one mirror surface located along the optical path between the light focusing and shaping mechanism and the optically transmissive substrate. In one embodiment, the light redirecting system is an oscillating mirror. In another embodiment, the light redirecting system is a rotating mirror. A transport mechanism moves the coated substrate relative to the projection system, such that the motion of the light redirection mechanism is synchronized with the motion of the transport mechanism. This synchronization results in the light from the light source being uniformly scanned across the second major surface of the coated substrate. The light focusing and shaping mechanism directs the light from the light source such that the light is focused at the mirror surface of the light redirecting mechanism.

The present invention is also directed toward a system for manufacturing a coated substrate. This manufacturing system includes a transport mechanism for transporting an optically transmissive substrate, having a first major surface and a second major surface, along a transport path between a source point and a destination point. The manufacturing system also includes a coating mechanism located along the transport path which dispenses an optically transmissive coating over the first major surface of the optically transmissive substrate, forming a coated substrate. A viewing screen is also included within the manufacturing system. The manufacturing system also includes an optical scanning assembly located along the transport path which enables inspection of the uniformity of the coating of the substrate on the viewing screen. Finally, the manufacturing system includes a drying mechanism which dries the optically transmissive coating on the top surface of the optically transmissive substrate.

The optical scanning assembly of the manufacturing system includes a light source which projects a scanning beam along an optical path. The optical scanning assembly also includes a light redirecting mechanism with one or more mirror surfaces, where the light redirecting mechanism redirects the laser beam at the viewing screen through the coated substrate. Finally, the optical scanning assembly includes a focusing and shaping mechanism which focuses and shapes the scanning beam from the light source such that the focal point of the scanning beam is at the mirror surface of the light redirecting mechanism. After hitting the mirror surface of the light redirection mechanism, the scanning beam is redirected through the coated substrate in an edge-to-edge scanning motion. The motion or speed of the scanning motion is adjusted for optimized operator visibility.

In one embodiment of the manufacturing system of the present invention, the optically transmissive substrate is made of transparent material, and the optically transmissive coating is translucent. The manufacturing system of the present invention works with both wet and dry coatings on the substrate. The light source employed within the projection system has a wavelength and intensity that does not interfere with the photosensitive qualities of the optically transmissive coating. In one embodiment of the present invention, the light source is a point light source, such as a laser.

The present invention is also directed toward a method for inspecting features of a coated substrate. As a first step in the method, an optically transmissive, coated substrate is transported between a source location and a destination location. As the substrate is transported, a light source is projected through the optically transmissive, coated substrate onto a viewing screen in optical alignment with the light source such that the viewing screen displays any irregularities in the coated substrate.

Finally, the present invention is directed toward an inspection system for viewing coated substrate features, where the inspection system is used during the manufacture of the coated substrate. The coated substrate passed through the inspection system is optically transmissive and has a first and second surface. The inspection system includes a projection system having a light assembly including a light source. The light source is positioned adjacent the first major surface, and a viewing screen is positioned adjacent the second major surface. The coated substrate is positioned in optical alignment along an optical path between the light assembly and the viewing screen, such that features in the coated substrate are usually observable on the viewing screen by an operator.

The present invention offers a manufacturing system having an inspection system for viewing substrate or coated substrate features. This inspection system enables an operator to quickly and easily detect surface irregularities on a coated substrate during the manufacturing process, resulting in a substantially reduced amount of waste product. The present invention is ideally suited for, but not limited to, the manufacture of photosensitive coatings, since the present invention employs a low intensity, controlled frequency light source which does not interfere with the photosensitive coating. Unlike prior art, hand-held light sources which could only check a small portion of the coated substrate at any given time, the present invention projects a rapidly scanning light source from edge-to-edge on the coated substrate such that an operator can simultaneously check the entire width of the coated substrate for surface irregularities at any given time.

BRIEF DESCRIPTION OF THE DRAWINGS

The accompanying drawings are included to provide a further understanding of the present invention and are incorporated in and constitute a part of this specification. The drawings illustrate the embodiments of the present invention and together with the description serve to explain the principles of the invention. Other embodiments of the present invention and many of the intended advantages of the present invention will be readily appreciated as the same become better understood by reference to the following detailed description when considered in connection with the accompanying drawings, in which like reference numerals designate like parts throughout the figures thereof, and wherein.

DETAILED DESCRIPTION

Figure 1:
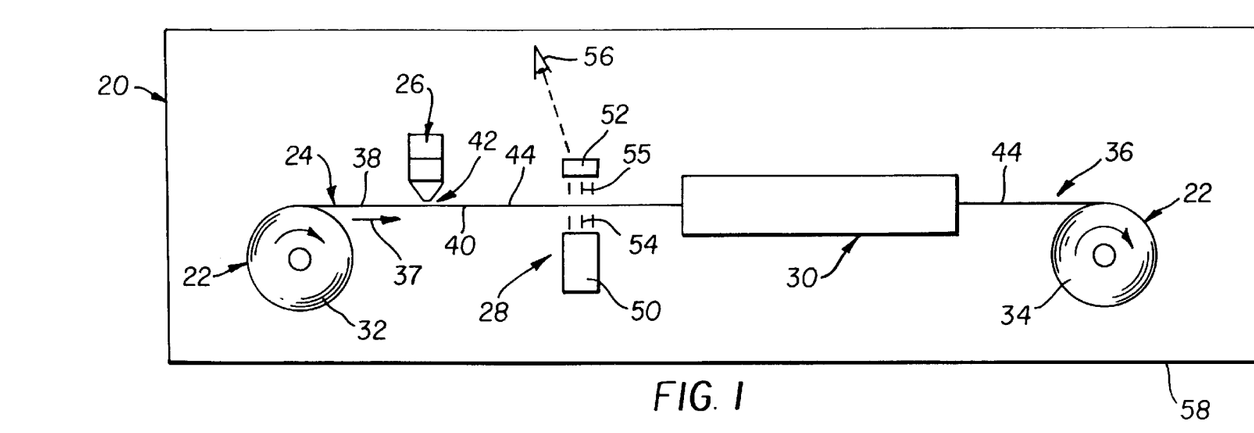
FIG. 1 is one exemplary embodiment of a system for manufacturing a coated substrate, including an inspection system for viewing coated substrate features, in accordance with the present invention.

In FIG. 1, a generalized illustration of one embodiment of a system for manufacturing a coated substrate (i.e., a coated web) in accordance with the present invention, including an inspection system for viewing coated substrate features, is indicated at 20. Although the embodiment shown is described in reference to a coated substrate process, the inspection system in accordance with the present invention can be employed for visual inspection of irregularities in a substrate or a coated substrate process.

In manufacturing system 20, the coating is wet at the time of inspection. The manufacturing system 20 includes a transport system 22, a substrate 24, a coating mechanism 26, an inspection system 28, and a dryer 30. The inspection system 28 in accordance with the present invention provides for visual inspection of substrate 24 after a coating is applied by coating mechanism 26 as it moves through the manufacturing system 20. The manufacturing system 20 in accordance with the present invention, including the unique inspection system 28, is described in further detail in the following paragraphs.

The transport system 22 moves the substrate 24 through the manufacturing system 20. In one embodiment of the present invention, the transport system 22 includes an unwinding roller 32 and a wind-up roller 34. The unwinding roller 32 contains a volume of the substrate 24 wound thereon prior to the manufacturing process. Wind-up roller 34 receives the substrate 24 after passing through the manufacturing process. In the exemplary embodiment shown, the substrate 24 (after coating and drying) is wound about the wind-up roller 34. The transport system 22 operates to move the substrate 24 along a transport path 36 (in a down web direction) between the unwinding roller 32 and the wind-up roller 34, indicated by arrow 37. The transport path 36 is defined by the manufacturing process as it moves between the unwinding roller 32 and the wind-up roller 34.

Substrate 24 (i.e., web) includes a first surface 38 and a second surface 40. Substrate 24 is at least partially optically transmissive, wherein substrate 24 allows light to pass therethrough. In one preferred embodiment, substrate 24 is substantially transparent.

Coating mechanism 26 is operably positioned along the transport path 36 adjacent first surface 38. Coating mechanism 26 operates to dispense (i.e., disperse) a wet coating, indicated at 42, on the first surface 38 of the substrate 24 as the substrate 24 moves along transport path 36 through the manufacturing system 20. Coating 42 is at least partially optically transmissive, wherein coating 42 allows light to pass therethrough. In one embodiment, coating 42 is substantially transparent. Substrate 21 and coating 42 form a coated substrate 44. Coated substrate 44 is also at least partially optically transmissive such that light can be transmitted through the coated substrate. Preferably, coated substrate 44 is substantially transparent or translucent.

The projection system for viewing features on coated substrates can be used to view any transparent or translucent coated substrate. The type of coating mechanism used in manufacturing system 20 in accordance with the present invention is not limited. Suitable manufacturing systems include, for example, die coating, extrusion coating, slide coating, curtain coating, roll coating, and gravure coating. Suitable coating mechanisms are described in *Modern Coating and Drying Technology*, eds. E. D. Cohen, and E. B. Gutoff, VCH Publishers, Inc., 1992 and are apparent to those skilled in the art. The projection system is especially useful in inspecting the manufacture of photosensitive substrates such as photothermographic and photographic elements. Such elements are often coated using extrusion coating and slide coating techniques. Such techniques are described in for example, in U.S. Pat. Nos. 4,977,852; 5,741,549; and 5,639,305.

Other suitable coating techniques will become apparent to those skilled in the art after reading the disclosure of the present application.

Next, coated substrate 44 passes though an inspection system 28. In one embodiment, the inspection system 28 comprises a projection system including a light source 50 and a viewing screen 52. The light source 50 is positioned adjacent the second surface 40 and the viewing screen 52 is positioned adjacent (i.e., operably near) the first surface 38. Optionally, light source 50 can be positioned adjacent first surface 38 and the viewing screen 52 can be positioned adjacent the second surface 40. Coated substrate 44 is positioned in optical alignment along an optical path 54 between the light source 50 and the viewing screen 52. When light source 50 is activated, light 55 is projected from light source 50 through coated substrate 44 onto the surface of viewing screen 52. Irregularities in the coating 42 are visually observed on the viewing screen 52 by operator or user 56 (represented by an "eye" in FIG. 1). The use of the terms "adjacent" or "operably near" are defined to mean that the viewing screen 52 is positioned a distance from coated substrate 44 which allows the irregularities to be visually observed on the viewing screen 52.

In one embodiment, coating 42 includes a photosensitive material (e.g., a photothermographic or a photographic film). The term "photosensitive material" as used herein is defined to include materials which react to or change state when exposed to light at a corresponding wavelength. Accordingly, manufacturing system 20 is employed under safe light conditions, indicated by line 58. As such, light source 50 provides light 55 for visual inspection having a wavelength and intensity which does not interfere with the photosensitive qualities of coating 42.

The inspection system 28 of the present invention allows an operator 56 to view the wet coated substrate 44 features as the substrate moves through the manufacturing process. Thus, any irregularities in coated substrate 44 can be detected immediately after coating mechanism 26 applies the coating 42 to substrate 24. The transport system 22 can move the coated substrate 44 through the manufacturing process at a very rapid rate. Inspection system 28 is operably positioned immediately following coating mechanism 26, providing immediate detection of any irregularities in coated substrate 44. This results in a significant reduction of unusable product. The inspection system of the present invention will be discussed in greater detail below.

Next, coated substrate 44 passes through a dryer 30. Dryer 30 operates to dry the wet coating 42 on the substrate 24. Dryer 30 may comprise single or multiple dryer mechanisms. In one preferred embodiment, dryer 30 includes an oven. Other drying mechanisms will become apparent to those skilled in the art after reading the disclosure of the present application. The coated substrate 44 is rolled onto a wind-up roller 34. Optionally, this process may be followed by a converting process which "converts" the coated substrate 44 into discrete units. Such discrete units can be packaged before being sold (e.g., rolls or sheets of film).

Figure 2:
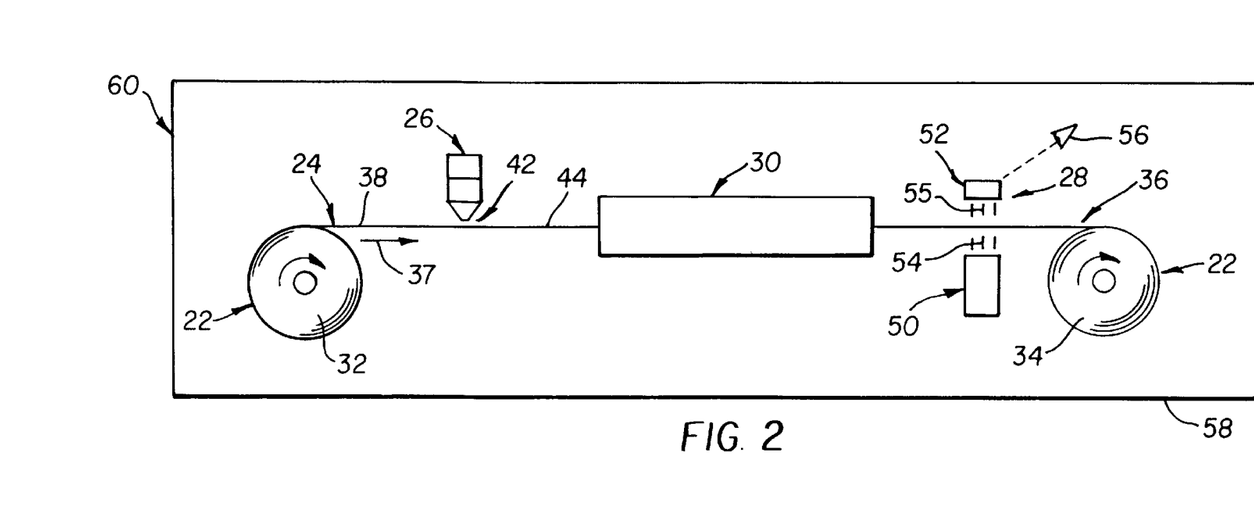
FIG. 2 is another exemplary embodiment of a system for manufacturing a coated substrate, including an inspection system for viewing coated substrate features, in accordance with the present invention.

The inspection system 28 in accordance with the present invention may be employed to visually inspect the coated substrate 44 when coating 42 is in a "wet" state or "dry" state. In FIG. 2, one alternative embodiment of a system for manufacturing a coated substrate 44 in accordance with the present invention, including an inspection system 28 for viewing coated substrate 44 features, is shown at 60. The manufacturing system 60 is similar to the manufacturing system 20 previously described herein. In the alternative embodiment shown, the inspection system 28 is positioned along the transport path 36 immediately following dryer 30. Accordingly, coating 42 on coated substrate 44 is dry as it passes through inspection system 28.

Figure 3:
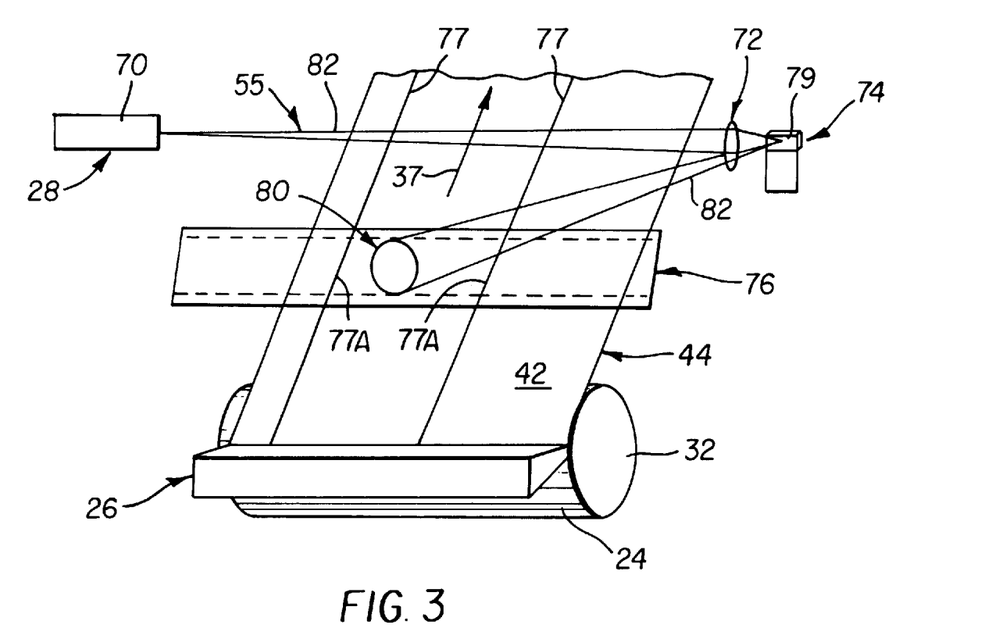
FIG. 3 is a perspective view illustrating one exemplary embodiment of an inspection system in accordance with the present invention.

In FIG. 3, one exemplary embodiment of inspection system 28 in accordance with the present invention is shown. The inspection system 28 is a projection system which includes a light source 70, focusing and shaping mechanism 72, light redirecting mechanism 74 and viewing screen 76. The projected irregularities on viewing screen 76 are indicated at 77A. Light source 70 projects beam of light 55 through coated substrate 44, projecting irregularities 77 in the coating 42 onto the viewing screen 76. Focusing and shaping mechanism 72 and light redirecting mechanism 74 are positioned along an optical path as defined by the light 55 between light source 70 and viewing screens 76. Focusing and shaping mechanism 72 and light redirecting mechanism 74 are positioned between light source 70 and coated substrate 44. Focusing and shaping mechanism 72 focuses and shapes the light beam 78 from light source 70 onto a mirror (i.e., reflective) surface 79 of the light redirecting mechanism 74, such that the focal point of the focusing and shaping mechanism 72 is at the mirror surface of light redirecting mechanism 74. After the redirected beam of light leaves light redirecting mechanism 74, the beam of light next passes through coated substrate 44 and is projected onto the surface of viewing screen 76, indicated at 80. Viewing screen 76 displays surface irregularities, indicated at 77A, within coating 42.

In one embodiment of the present invention, light source 70 is a point light source. A point light source provides the advantage of being well defined and well controlled at the point of origin. In one preferred embodiment, the point light source is a laser. The laser has the advantage of being well focused and wavelength limited. Thus, if the substrate coating 42 is photosensitive, the wavelength of the laser is chosen as to not interfere with the photosensitive qualities of the substrate coating. Similarly, the voltage of the laser must be chosen such that it doesn't interfere (i.e., affect) the photosensitive coated substrate. For example, a higher power laser may result in high visibility of defects projected into viewing screen 76. In one aspect, the laser is an 8.5 milliwatt laser which provides a laser beam 82 having a wavelength of approximately 532 nanometers. In another aspect, the laser is a 50 milliwatt laser.

Light source 70 provides a controlled (e.g., collimated) laser beam 82. Laser light source 70 also has the advantage of making phase type variations in the surface of coating 42 (e.g., surface irregularities, such as variations in coating thicknesses) more visible on viewing screen 76. Phase type variations in coated substrate 44 cause the coated substrate 44 to act in a lens/prism like fashion, wherein the variations in the thickness of the coating causes light to deflect differently such that well defined dark and light areas are visible on viewing screen 46 (as irregularities 77).

In one embodiment, focusing and shaping mechanism 72 is a lens assembly which focuses the beam from light source 70 onto mirror surface 79 of light redirecting mechanism 74. Preferably, the lens assembly comprises one or more lenses positioned along the optical path. In one embodiment, focusing and shaping mechanism 72 is a spherical lens, such as a double convex lens.

In one embodiment of the present invention, light redirecting mechanism 74 is a motorized scan mirror. In a preferred embodiment, the scan mirror is a single-faceted oscillating mirror which sits on a suspension mechanism and oscillates back and forth. The scan mirror operates to scan laser beam 82 back and forth (i.e., edge-to-edge) across second surface 40 and viewing screen 76. In one preferred embodiment, the oscillating frequency (i.e., scan rate) is 90 hertz. In an alternative embodiment, the scan mirror is a rotating mirror. The oscillating mirror includes a mirrored surface 79 which is highly reflective. In one embodiment, the scan mirror is mechanically coupled to a motor shaft (not shown), and oscillated or roated via a motor mechanism coupled to the motor shaft.

The oscillation of the mirror in the preferred embodiment is at a rate such that the redirected scan beam from the light redirecting mechanism 74 uniformly scans through coated substrate 44 in an edge-to-edge motion, and appears as a constant light to the operator. The edge-to-edge motion is substantially crosswise relative to the direction of movement of the coated substrate 44. As the redirected scan beam 82 emerges from the first surface 38 of coated substrate 44, it is projected onto viewing screen 76. The operator 56 can now examine the full web image projected onto viewing screen 76 for features such as fine streaks and mottle and take corrective action (i.e., adjust the manufacturing system 20) if necessary. The present invention allows the operator to view the entire edge-toedge surface of coated substrate 44 at one time. Also, the present invention provides superior illumination of surface irregularities on coated substrate 44 so that an operator can better judge the severity of the irregularities and make a better (i.e., informed) decision on whether corrective action is necessary.

Figure 4:
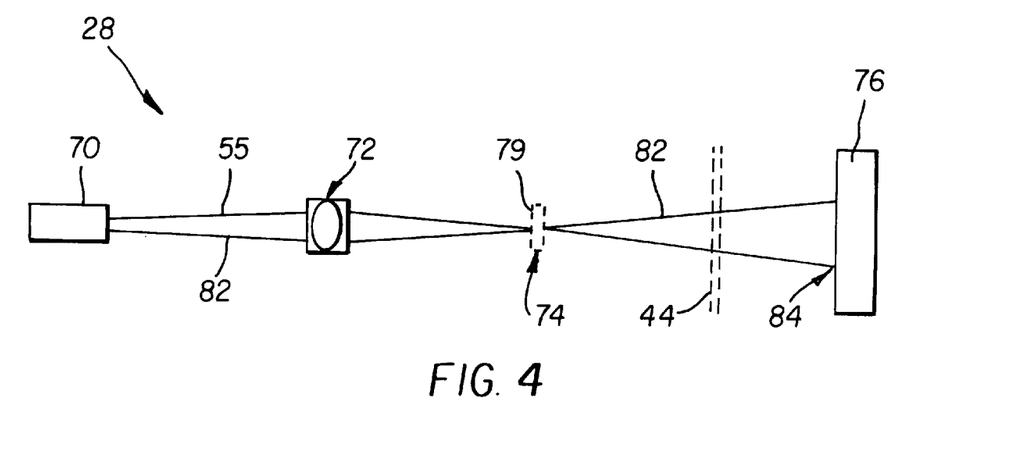
FIG. 4 is an optical diagram illustrating one exemplary embodiment of an optical path of the light source used within an inspection system in accordance with the present invention.

FIG. 4 is an illustration of the optical path of the light source used within the inspection system 28 of the present invention. Light source 70 directs light beam 82 toward focusing and shaping mechanism 72. Focusing and shaping mechanism 72 focuses and shapes the light beam toward light redirection mechanism 74 such that the focal point of the light beam is at mirror surface 79 of the light redirection mechanism 74. Light redirection mechanism 74 redirects the light beam through the coated substrate 44 and onto a surface of viewing screen 76. The light beam must expand off light redirection mechanism 74 such that a spot of light 84 projected on the viewing screen provides a substantial viewing region (e.g., 4 to 5 inches in diameter). This is necessary so that the image is large enough to allow an operator to recognize features or irregularities such as streaks.

Figure 5:
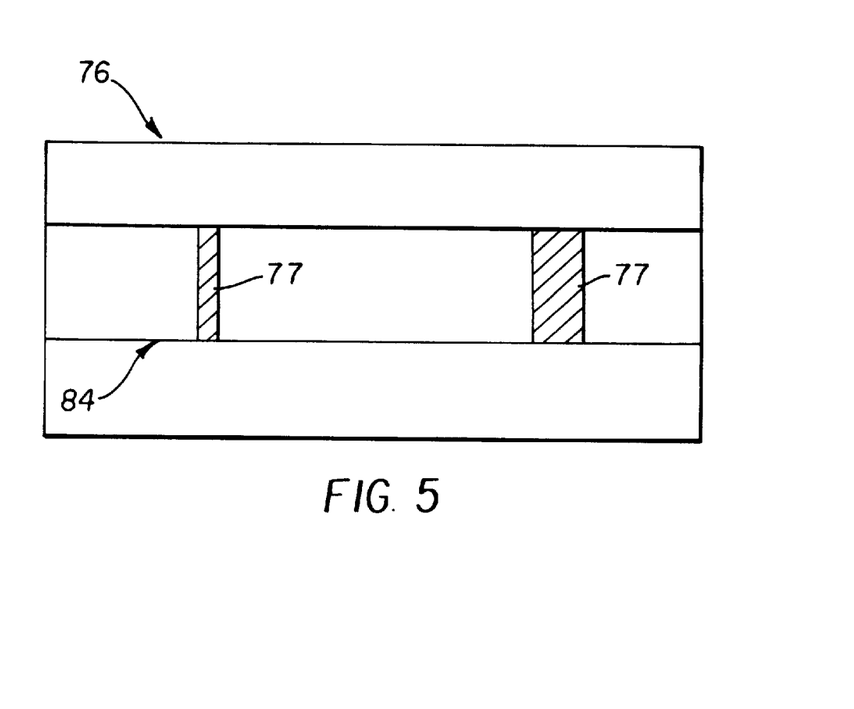
FIG. 5 is a front view illustration of one exemplary embodiment of a viewing screen used in an inspection system in accordance with the present invention, wherein irregularities in a coated substrate are projected onto the viewing screen.

FIG. 5 is a front view illustration of the viewing screen 76 of the present invention, wherein irregularities 77 in the coated substrate 44 are projected onto the viewing screen 76 (indicated at 77A). Surface irregularities 77 on coated substrate 44 are visible on viewing screen 76, since the surface irregularities refract the projected light at a rate different than the rest of coated substrate 44. In one aspect, a considerable amount of light is diffusely scattered by coated substrate 44, so the coated substrate 44 to viewing screen 76 distance should be long enough to reduce the amount of diffuse light reaching the viewing screen 76, resulting in an image having enhanced viewability. In one embodiment, viewing screen 76 is positioned approximately 2 feet away from coated substrate 44, and the image size of the light beam 82 reaching the viewing screen 76 is about 4 to 5 inches in diameter. This relatively large image size will enable an operator to recognize undesirable features such as streaks on viewing screen 76.

Viewing screen 76 is a transmissive surface, such as a thin diffusing film, on which the image of the coated substrate is visible. The sharpest viewing image is achieved by using a thinner diffusing film for viewing screen 76. Other traditional screen materials may be used for viewing screen 76. However, while the image on the other traditional viewing screen materials is brighter, some of the image sharpness may be lost due to the diffusion of the light within the increased thickness of these materials. Suitable viewing screens will become apparent to those skilled in the art after reading the disclosure of the present invention.

In one exemplary embodiment, the inspection system in accordance with the present invention is used as part of a system for manufacturing a photosensitive film. The photosensitive film includes a clear plastic substrate having a photosensitive coating thereon. In one exemplary embodiment, the clear plastic substrate is 0.005 of an inch thick and the photosensitive coating is 0.001 of an inch thick. The photosensitive coating is at least partially clear and partially diffusing. The manufacturing process manufactures the coated substrate in widths up to 60 inches wide, with lengths 5000 feet ±1000 feet. The coated substrate is manufactured at a typical speed 100 to 400 feet per minute. After manufacturing, the coated substrate is cut for a desired format (e.g., 8"×10", 17"×14" etc.) and packaged.

The inspection system includes a light source comprising an 8.5 milliwatt laser which provides a laser beam having a wavelength of approximately 532 nonometers. The light redirecting mechanism includes a single faceted mirror, wherein the focal point of the laser beam is at the mirror surface. The mirror is positioned approximately 60 inches from the clear plastic substrate. The viewing screen is positioned approximately 36 inches from the photosensitive coating. The laser beam is projected through the coated substrate onto the viewing screen, being scanned at a rate of 90 hertz, such that it appears to the operator as a constant light source. This example resulted in clear viewing of coated substrate features or irregularities on the viewing screen by an operator.

In one embodiment, the aforementioned example using an inspection system in accordance with the present invention is used as part of a manufacturing process for the manufacture of medical imaging film commercially available under the tradename DryView(™) Medical Imaging Film, commercially available from Imation Corporation of St. Paul, Minn.

Similar materials are typically prepared on substrates having a thickness of from 0.004 to 0.007 inch (102 microns to 178 microns) and have coatings of 0.001 inch (25 microns). Materials of this type arc typically manufactured at coating speeds of from 100 to 400 feet per minute (30.5 meters/min to 122 meters/min).

Numerous characteristics and advantages of the invention have been set forth in the foregoing description. It will be understood, of course, that this disclosure is, and in many respects, only illustrative. Changes can be made in details, particularly in matters of shape, size and arrangement of parts without exceeding the scope of the invention. For example, as described herein the inspection system in accordance with the present invention can be used to visually inspect features in substrate processes or coated substrate processes. For coated substrate processes, the viewing screen my be optionally located adjacent the substrate and the light source may be located adjacent the substrate coating. The invention scope is defined in the language in which the appended claims are expressed.

We claim:

1. An inspection system for viewing substrate features in a manufacturing process, wherein the substrate is a moving optically transmissive substrate having a first major surface and a second major surface, the system comprising:

a projection system including a collimated light source positioned adjacent the second major surface, a light redirection mechanism, and a viewing screen positioned adjacent the first major surface, wherein the substrate is positioned in optical alignment along an optical path between the redirection mechanism and the viewing screen, light from the collimated light source being focused at a reflective surface of the light redirection mechanism, the light diverging off of the reflective surface to provide an enlarged spot of light transmitted through the optically transmissive substrate and appearing on the viewing screen as a full width projection of the substrate where irregularities in the surface can be visually observed.

2. The system of claim 1, wherein the optically transmissive substrate is transparent.

3. The system of claim 1, further comprising an optically transmissive coating disposed over the first major surface of the optically transmissive substrate, forming a coated substrate.

4. The system of claim 3, wherein the optically transmissive coating is wet.

5. The system of claim 3, wherein the optically transmissive coating is dry.

6. The system of claim 3, wherein the optically transmissive coating is photosensitive.

7. A manufacturing system having an inspection system for viewing coated substrate features, comprising:

an optically transmissive substrate having a first major surface and a second major surface;

an optically transmissive coating disposed over the first major surface of the optically transmissive substrate, forming a coated substrate; and a projection system including a collimated light source positioned adjacent the second major surface, a light redirection mechanism, and a viewing screen positioned adjacent the first major surface, wherein the coated substrate is positioned in optical alignment along an optical path between the light redirection mechanism and the viewing screen, light from the collimated light source being focused at a reflective surface of the light redirection mechanism, the light diverging off of the reflective surface to provide an enlarged spot of light transmitted through the optically transmissive substrate and appearing on the viewing screen as a full width projection of the coated substrate where irregularities in the coated top surface can be visually observed by a user.

8. The system of claim 7, wherein the optically transmissive substrate is transparent.

9. The system of claim 7, wherein the optically transmissive coating is translucent.

10. The system of claim 7, wherein the optically transmissive coating is wet.

11. The system of claim 7, wherein the optically transmissive coating is dry.

12. The system of claim 7, wherein the optically transmissive coating is photosensitive.

13. The system of claim 12, wherein the light source has a wavelength and/or an intensity that does not interfere with the photosensitive qualities of the optically transmissive coating.

14. The system of claim 7, wherein the optically transmissive coating is a photothermographic coating.

15. The system of claim 7, wherein the optically transmissive coating is a photographic coating.

16. The system of claim 7, wherein the light source is a point light source.

17. The system of claim 16, wherein the point light source is a laser.

18. The system of claim 7, wherein the system further includes a light focusing and shaping mechanism located along the optical path between the light source and the coated substrate.

19. The system of claim 18, wherein the light focusing and shaping mechanism is a set of one or more optical lenses.

20. The system of claim 19, wherein the set of one or more optical lenses is a double convex lens.

21. The system of claim 18, wherein the light redirecting mechanism includes at least one mirror surface located along the optical path between the light focusing and sharping mechanism and the optically transmissive substrate.

22. The system of claim 21, wherein the light redirecting mechanism is an oscillating mirror.

23. The system of claim 21, wherein the light redirecting mechanism is a rotating mirror.

24. The system of claim 21, wherein the system further includes a transport mechanism for moving the coated substrate relative to the projection system.

25. The system of claim 24, wherein the light redirection mechanism is operated at a speed which scans the light from the light source uniformly across the second major surface of the moving coated substrate such that it appears to be constant illumination.

26. The system of claim 25, wherein the light focusing and shaping mechanism directs the light from the light source such that the light has a focal point at the mirror surface of the light redirecting mechanism.

27. A manufacturing system having an inspection system for viewing coated substrate features, comprising:
an optically transmissive substrate having a first major surface and a second major surface;
an optically transmissive coating disposed over the first major surface of the optically transmissive substrate, forming a coated substrate; and
a projection system including a collimated light source positioned adjacent the first major surface, a light redirection mechanism, and a viewing screen positioned adjacent the second major surface, wherein the coated substrate is positioned in optical alignment along an optical path between the light redirection mechanism and the viewing screen, light from the collimated light source being focused at a reflective surface of the light redirection mechanism, the light diverging off of the reflective surface to provide an enlarged spot of light transmitted through the optically transmissive substrate and appearing on the viewing screen as a full width projection of the coated substrate where irregularities in the coated top surface can be visually observed by a user.

28. A system for manufacturing a coated substrate, the system comprising:
an optically transmissive substrate having a first major surface and second major surface;
a transport mechanism for transporting the optically transmissive substrate, along a transport path between an origin point and a destination point;
a coating mechanism located along the transport path which dispenses optically transmissive coating over the first major surface of the optically transmissive substrate, forming a coated substrate;
a viewing screen;
an optical scanning assembly located along the transport path and projecting an enlarged spot of light through the substrate and the coating, the enlarged spot light yielding what appears as a full width projection of the coated substrate which enables visual inspection of the uniformity of the coating of the substrate on the viewing screen; and
a drying mechanism which dries the optically transmissive coating on the top surface of the optically transmissive substrate, inspection by the optical scanning assembly taking place prior to the drying mechanism.

29. The manufacturing system of claim 28, wherein the optical scanning assembly further includes:
a light source which projects a scanning beam along an optical path;
a light redirecting mechanism having at least one mirror surface, wherein said light redirecting mechanism is in motion with the transport mechanism; and
a focusing and shaping mechanism which focuses and shapes the scanning beam from the light source such that a focal point of the scanning beam is at the mirror surface of the light redirecting mechanism, wherein after hitting the mirror surface, the scanning beam expands and is redirected through the coated substrate in an edge-to-edge scanning motion yielding what visually appears as a full width projection of the coated substrate.

30. The manufacturing system of claim 28, wherein the optically transmissive substrate is transparent.

31. The manufacturing system of claim 28, wherein the optically transmissive coating is wet.

32. The manufacturing system of claim 28, wherein the optically transmissive coating is dry.

33. The manufacturing system of claim 28, wherein the optically transmissive coating is photosensitive.

34. The manufacturing system of claim 33, wherein the scanning beam has a wavelength and intensity that does not interfere with the photosensitive qualities of the optically transmissive coating.

35. The manufacturing system of claim 28, wherein the light source is a point light source.

36. The manufacturing system of claim 35, wherein the point light source is a laser.

37. A method for inspecting features of a coated substrate, comprising the steps of:
transporting an optically transmissive, coated substrate along a transport path between a source location and a destination location;
focusing collimated light from a light source onto a reflective surface, the collimated light diverging upon reflecting from the reflective surface; and
directing the diverging light through the optically transmissive, coated substrate onto a viewing screen in optical alignment with the light source yielding what visually appears as a full width projection of the coated substrate, wherein the viewing screen displays irregularities in the coated substrate.

38. An inspection system for viewing coated substrate features, wherein the inspection system is used during the manufacture of the coated substrate, wherein the coated substrate is substantially optically transmissive and includes a first major surface and a second major surface, the inspection system comprising:
a projection system including a light assembly having a collimated light source positioned adjacent the first major surface, a light redirection mechanism, and a viewing screen positioned adjacent the second major surface, wherein the coated substrate is positioned in optical alignment along an optical path between the light redirection mechanism and the viewing screen, light from the collimated light source being focused at a reflective surface of the light redirection mechanism, the light reflecting off of the reflective surface to provide a diverging light transmitted through the optically transmissive substrate and yielding what visually appears as a full width projection of the coated substrate wherein features in the coated substrate are visually observable on the viewing screen by an operator.

39. The inspection system of claim 38, wherein the coated substrate includes a coating layer and a substrate, and wherein the first major surface is a coating surface and the second major surface is a substrate surface.

40. The inspection system of claim 39, wherein the coating layer is wet.

41. The inspection system of claim 39, wherein the coating layer is dry.

42. The inspection system of claim 38, wherein the light assembly is an optical scanning assembly, and the light source is a laser.

* * * * *